US009770181B2

(12) United States Patent
Kurzweil et al.

(10) Patent No.: US 9,770,181 B2
(45) Date of Patent: *Sep. 26, 2017

(54) SYSTEMS AND ASSOCIATED METHODS FOR USE OF PATTERNS IN PROCESSING ON MOBILE MONITORING DEVICE

(71) Applicant: Medicomp, Inc., Melbourne, FL (US)

(72) Inventors: Raymond C. Kurzweil, Newton, MA (US); Paul Albrecht, Bedford, MA (US); Lucy Gibson, Belmont, MA (US)

(73) Assignee: Medicomp, Inc., Melbourne, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/253,401

(22) Filed: Aug. 31, 2016

(65) Prior Publication Data

US 2016/0367160 A1    Dec. 22, 2016

Related U.S. Application Data

(63) Continuation of application No. 14/592,581, filed on Jan. 8, 2015, now Pat. No. 9,445,736, which is a
(Continued)

(51) Int. Cl.
*A61B 5/0402* (2006.01)
*A61B 5/0452* (2006.01)
(Continued)

(52) U.S. Cl.
CPC .......... *A61B 5/0402* (2013.01); *A61B 5/0006* (2013.01); *A61B 5/0008* (2013.01);
(Continued)

(58) Field of Classification Search
None
See application file for complete search history.

(56) References Cited

U.S. PATENT DOCUMENTS

| 3,442,264 A | 5/1969 | Levitt |
| 5,421,830 A | 6/1995 | Epstein et al. |

(Continued)

OTHER PUBLICATIONS

S. Rhee & S. Liu, Dept. of Mech. Eng., MIT, Cambridge, MA, USA, "An Ultra-Power, Self-Organizing Wireless Network and Non-Invasive Biomedical Instrumentation", 2002, Engineering in Medicine and Biology, $24^{th}$ Annual Conference and the Annual Fall Meeting of the Biomedical Engineering Society Conference, vol. 3, Conference Date—Oct. 23-26, 2002, pp. 1803-1804, <ieeexplore.ieee.org/document/1053033/> (3 Pages).

(Continued)

*Primary Examiner* — Kennedy Schaetzle
(74) *Attorney, Agent, or Firm* — Mark Malek; Kelly G. Swartz; Widerman Malek, PL

(57) ABSTRACT

An arrangement may include a first system provided by a mobile device for processing physiological data representative of a beating heart. The mobile device may be adapted to execute a process for using at least one pattern to detect a notable finding in the physiological data and for sending the notable finding to a second system. The second system may be adapted to execute a process for analyzing the notable finding, for determining at least one new pattern to send to the mobile device, and for sending the at least one new pattern to the mobile device. The at least one new pattern may also include a rule that includes a set of conditions and an action to perform if the set of conditions is met.

22 Claims, 5 Drawing Sheets

Related U.S. Application Data continuation of application No. 13/525,503, filed on Jun. 18, 2012, now Pat. No. 8,954,137, which is a continuation of application No. 11/136,338, filed on May 24, 2005, now Pat. No. 8,204,580.

(60) Provisional application No. 60/574,268, filed on May 25, 2004.

(51) Int. Cl.
| | |
|---|---|
| *A61B 5/00* | (2006.01) |
| *A61B 5/04* | (2006.01) |
| *A61B 5/0404* | (2006.01) |
| *A61B 5/0432* | (2006.01) |
| *A61B 5/0205* | (2006.01) |
| *A61B 5/0476* | (2006.01) |
| *A61B 5/0488* | (2006.01) |

(52) U.S. Cl.
CPC .......... *A61B 5/0205* (2013.01); *A61B 5/0404* (2013.01); *A61B 5/04012* (2013.01); *A61B 5/0432* (2013.01); *A61B 5/0452* (2013.01); *A61B 5/0476* (2013.01); *A61B 5/0488* (2013.01); *A61B 5/04525* (2013.01); *A61B 2560/0271* (2013.01)

(56) References Cited

U.S. PATENT DOCUMENTS

| | | | |
|---|---|---|---|
| 5,544,661 | A | 8/1996 | Davis et al. |
| 5,966,692 | A | 10/1999 | Langer et al. |
| 6,073,046 | A | 6/2000 | Patel et al. |
| 6,261,230 | B1 | 7/2001 | Bardy |
| 6,270,457 | B1 | 8/2001 | Bardy |
| 6,280,380 | B1 | 8/2001 | Bardy |
| 6,364,834 | B1 | 4/2002 | Reuss et al. |
| 6,485,418 | B2 | 11/2002 | Yasushi et al. |
| 6,544,173 | B2 | 4/2003 | West et al. |
| 6,544,174 | B2 | 4/2003 | West et al. |
| 6,594,523 | B1 | 7/2003 | Levine |
| 6,609,023 | B1 | 8/2003 | Fischell et al. |
| 6,804,558 | B2 | 10/2004 | Haller et al. |
| 6,945,934 | B2 | 9/2005 | Bardy |
| 7,181,505 | B2 | 2/2007 | Haller et al. |
| 7,343,197 | B2 | 3/2008 | Shusterman |
| 7,715,905 | B2 | 5/2010 | Kurzweil et al. |
| 8,483,807 | B2 | 7/2013 | Kurzweil et al. |
| 8,954,137 | B2 * | 2/2015 | Kurzweil ............ A61B 5/0452 600/515 |
| 9,445,736 | B2 * | 9/2016 | Kurzweil ............ A61B 5/0452 |
| 2002/0052539 | A1 | 5/2002 | Haller et al. |

OTHER PUBLICATIONS

EP Lab Digest, "Cardiac Surveillance at Home", Nov. 2002, vol. 2—Issue 11, <www.eplabdigest.com/article/1137> (4 Pages).
Welch Allyn Inc., "CardioPerfect PC-Based Resting ECG, The Perfect Choice", 2003, <https://intl.welchallyn.com/cardiopulmonary/English/RestingEcg/product brochure/CC Resting ECG.pdf> (2 Pages).
PR Newswire, "Medical Intelligence—A Quebec Firm Invents the VPS, a Revolutionary Wireless Portable Automatic Cardiac Alert System", Nov. 12, 2003, NewsRoom, Westlaw Thomas Reuters. (3 Pages).
Circuit Cellar the Magazine, "Remote Health-Monitoring System", Jun. 2003, vol. 2—Issue No. 155 (100 Pages) pp. 10-17 Relevant.
Steven A. Rothman, M.D., et al. "The Diagnosis of Cardiac Arrhythmias: A Prospective Multi-Center Randomized Study Comparing Mobile Cardiac Outpatient Telemetry Versus Standard Loop Event Monitoring", Mar. 2007, J Cardiovasc Electrophysiol, vol. 18. (7 Pages).
Maude, "U.S. Food and Drug Administration, Manufacturer User Facility and Distributor Experience, Cardionet Mobile Cardiac Outpatient Telemetry", Dec. 4, 2008, Westlaw Thomas Reuters. (2 Pages).
Business Wire, Spacelabs Medical Receives FDA Approval for New Wireless, Multi-Parameter Waveform Clinical Messenger., Jan. 19, 2000, Business Wire (2 Pages).
USPTO, Final Office Action dated Nov. 28, 2007 for issued U.S. Pat. No. 8,204,580. (9 Pages).
Applicant, Response After Final Office Action dated May 23, 2008 for issued U.S. Pat. No. 8,204,580. (8 Pages).
USPTO, Advisory Action dated Jun. 11, 2008 for issued U.S. Pat. No. 8,204,580. (2 Pages).
Applicant, Appeal Brief dated Aug. 25, 2008 or issued U.S. Pat. No. 8,204,580. (28 Pages).
USPTO, Examiner's Answer to Appeal Brief dated Dec. 3, 2008 for issued U.S. Pat. No. 8,204,580. (19 Pages).
Applicant, Reply to Examiner's Answer dated Feb. 2, 2009 for issued U.S. Pat. No. 8,204,580. (14 Pages).
USPTO, Advisory Action dated Apr. 14, 2009 for issued U.S. Pat. No. 8,204,580. (12 Pages).
Applicant, Reply Brief to Examiner's Supplemental Answer dated Jul. 7, 2009 for issued U.S. Pat. No. 8,204,580. (16 Pages).
USPTO, Advisory Action dated Sep. 21, 2009 for issued U.S. Pat. No. 8,204,580. (2 Pages).
USPTO, Patent Board Decision—Examiner Reversed dated Nov. 1, 2011 for issued U.S. Pat. No. 8,204,580. (5 Pages).
Applicant, Terminal Disclaimer dated Feb. 1, 2012 for issued U.S. Pat. No. 8,204,580. (2 Pages).
USPTO, NonFinal Office Action dated Jun. 15, 2007 for issued U.S. Pat. No. 8,204,580. (7 Pages).
Applicant, Response to Non-Final Office Action dated Sep. 14, 2007 for issued U.S. Pat. No. 8,204,580. (10 Pages).
USPTO, Notice of Allowance dated Feb. 22, 2012 for issued U.S. Pat. No. 8,204,580. (3 Pages).
USPTO, NonFinal Office Action dated Jan. 14, 2014 for issued U.S. Pat. No. 8,954,137. (12 Pages).
Applicant, Response to Non-Final Office Action dated Apr. 14, 2014 for issued U.S. Pat. No. 8,954,137. (18 Pages).
USPTO, Final Office Action dated Jun. 26, 2014 for issued U.S. Pat. No. 8,954,137. (9 Pages).
Applicant, Response After Final Office Action dated Sep. 24, 2014 for issued U.S. Pat. No. 8,954,137. (7 Pages).
USJPTO, Notice of Allowance dated Jan. 8, 2015 for issued U.S. Pat. No. 8,954,137. (5 Pages).
USPTO, Non-Final Office Action dated Jan. 6, 2016, for U.S. Appl. No. 14/592,581. (7 Pages).
Applicant, Response to Non-Final Office Action dated Feb. 26, 2016 for U.S. Appl. No. 14/592,581. (5 Pages).
USPTO, Final Office Action dated Mar. 28, 2016 for U.S. Appl. No. 14/592,581. (8 Pages).
Applicant, Response After Final Office Action dated May 10, 2016 for U.S. Appl. No. 14/592,581. (4 Pages).
Uspto, Notice of Allowance dated May 20, 2016 for U.S. Appl. No. 14/592,581.

* cited by examiner

SYSTEMS AND ASSOCIATED METHODS FOR USE OF PATTERNS IN PROCESSING ON MOBILE MONITORING DEVICE

RELATED APPLICATIONS

This application is a continuation and claims the benefit under 35 U.S.C. §120 of pending U.S. patent application Ser. No. 14/592,581, titled Use of Patterns in Processing on Mobile Monitoring Device and Computer System filed by the inventor of the present application on Jan. 8, 2015, which, in turn, is a continuation and claims the benefit under 35 U.S.C. §120 of pending U.S. patent application Ser. No. 13/525,503, titled Use of Patterns in Processing on Mobile Monitoring Device and Computer System, filed by the inventor of the present application on Jun. 18, 2012, which has subsequently issued as U.S. Pat. No. 8,954,137 on Feb. 10, 2015, and which, in turn, is a continuation and claims the benefit under 35 U.S.C. §120 of U.S. patent application Ser. No. 11/136,338, titled Use of Patterns in Processing on Mobile Monitoring Device and Computer System, filed May 24, 2005 by the inventor of the present application, which has subsequently issued as U.S. Pat. No. 8,204,580 on Jun. 19, 2012, and which, in turn, claims the benefit under 35 U.S.C. §119(e) of U.S. Provisional Patent Application Ser. No. 60/574,268, titled Wireless ECG Mobile Device That Communicates With A Base Station, filed by the inventor of the present application on May 25, 2004, the entire contents of each of which are incorporated herein by reference.

FIELD OF THE INVENTION

The present invention relates to systems and methods for monitoring physiological characteristics of ambulatory patients.

BACKGROUND

In Holter monitoring, a patient module acquires and records ECG data but does not analyze the data. After recording is complete, data is transferred from the patient module to a base station that analyzes the data. The base station identifies clinically notable findings for review by clinical specialists. In "event monitoring" data selection is performed in the patient module, either as the result of ECG analysis or due to a patient-initiated trigger. Selected ECG results are transmitted or downloaded to a system at a central facility.

U.S. Pat. No. 6,694,177 B2 by Eggers et al. entitled Control Of Data Transmission Between A Remote Monitoring Unit And A Central Unit describes bidirectional communications between a remote monitoring unit and a central unit. The remote monitoring unit obtains a monitored data set from the patient, analyzes the monitored data set to obtain a derived data set and determines from the derived data set that communication with the central unit is required. The central unit analyzes the initially transmitted data set and instructs the remote monitoring unit to transmit an additional data set related to the monitored data set and a time when to transmit the additional transmitted data set.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention are related to a system that may include circuitry to receive information from a mobile device including physiological data such as ECG data representative of a beating heart, circuitry to analyze the physiological data using at least one pattern to detect a notable finding in the physiological data, circuitry to determine at least one pattern to send to the mobile device based on the analysis of the physiological data, and circuitry to send the at least one determined pattern to the mobile device.

The following are within the scope of the claim. The determined pattern may include the parameters of a mathematical model. The determined pattern may include a template derived from historical physiological data. The circuitry to analyze the physiological data may include circuitry to compare the analyzed physiological data to templates from categories of physiological events in order to classify the physiological data. The determined pattern may include sending software. The pattern may be a cardiac rhythm pattern. The cardiac rhythm pattern may be a "bigeminy" rhythm that may be defined as having alternating normal "N" and ventricular "V" beats, the pattern including a rhythm template that may represent the bigeminy pattern as eight (8) beats of (N V N V N V N V) and wherein incoming beats may be compared to the bigeminy template to determine if a bigeminy condition exists in signals of the incoming beats.

The pattern may be selected based on information from the mobile device, including user characteristics or physiological data samples collected for the user from the mobile device, or data derived by the mobile device from the physiological data samples, including heart beat patterns and heart rhythm patterns. The pattern may be selected based on user characteristics, including patient clinical and demographic information, and may be sent to initialize the mobile device. The pattern may be new or updated software for execution by the mobile device. The pattern may be a rule that has a set of conditions and an action to perform if the set of conditions is met. The rule may be a classification rule. The rule may be a processing rule. The set of rules may be generated for a specific condition or patient.

According to an additional aspect of the invention, an arrangement may include a mobile device for processing physiological data such as ECG data representative of a beating heart using at least one pattern to detect a notable finding in the physiological data, sending the physiological data corresponding to the notable finding to a second system, and the second system executing a process for analyzing the physiological data corresponding to the notable finding and determining at least one new pattern to send to the mobile device based on the analysis of the physiological data. The arrangement also may include a process to send the at least one one determined pattern to the mobile device.

According to an additional aspect of the invention, a method may include receiving information from a mobile device including physiological data such as ECG data representative of a beating heart, analyzing the physiological data using at least one pattern to detect a notable finding in the physiological data, determining at least one pattern to send to the mobile device based on analyzing the physiological data, and sending the at least one determined pattern to the mobile device.

A pattern may be a specification of characteristics, i.e., a form or model that may be used by the mobile device and the second computer system to compare to incoming physiological data. For example, and without limitation, a pattern may include new or updated software for execution by the mobile device. Patterns may be represented as events in time. A pattern may be any specification of characteristics or a set of parameters. A pattern may be a rule that has a set of conditions and an action that may be performed if the set of conditions is met. Patterns may be used to affect subsequent processing by the mobile device. Thus, the second computer system may modify operation of the mobile device by changing new or revised patterns.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

Figure 1:
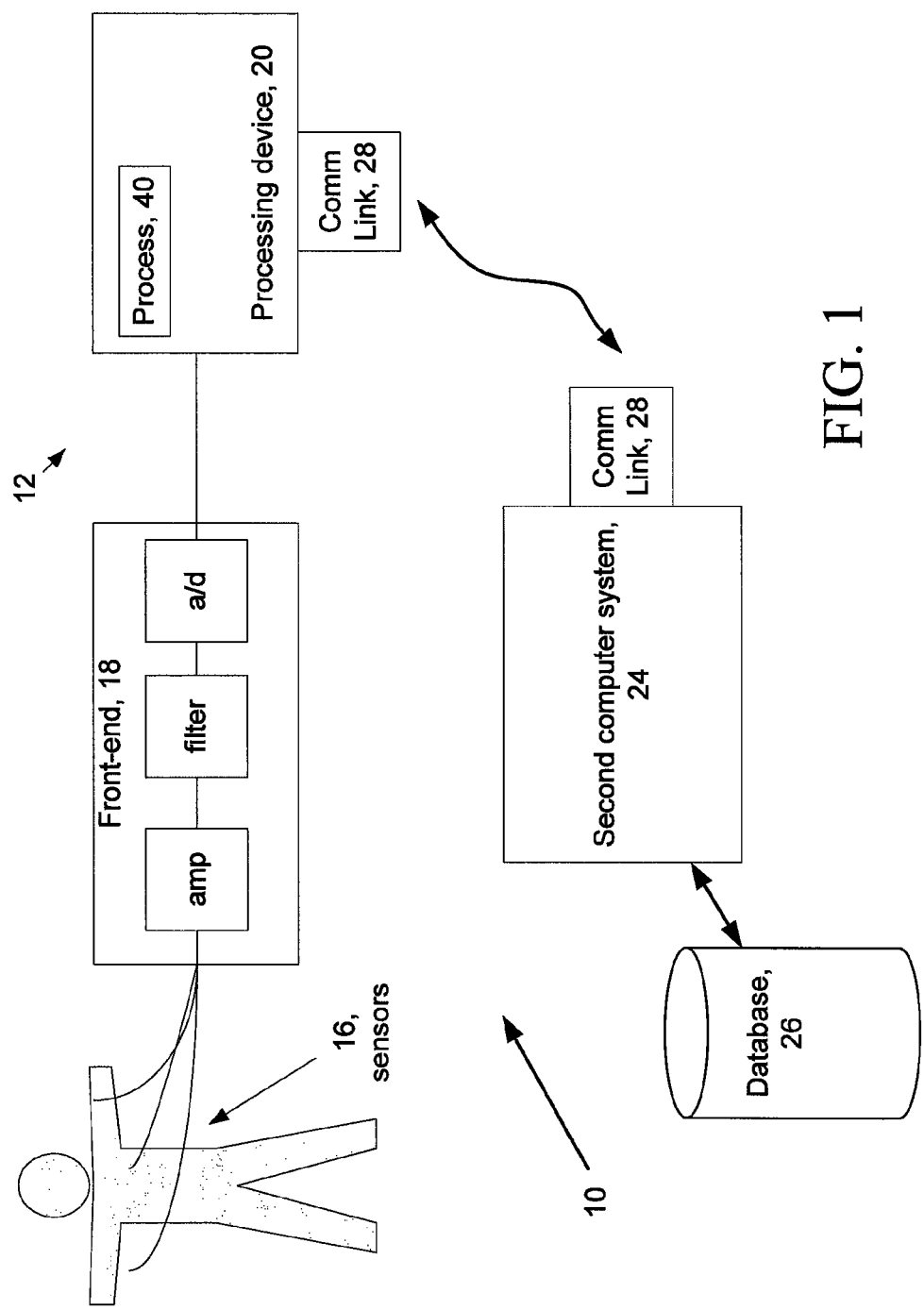
FIG. 1 is a block diagram of a system for patient monitoring and analysis.

Referring to FIG. 1, a system arrangement 10 may include physiological sensors 16 connected to a mobile patient device 12 that may collect, process, and record findings from physiological data that may be provided from the sensors 16. The mobile patient device 12 may include a mobile processing device 20 that may execute a process 40 that determines notable findings in real time and sends the notable findings over a communication link 28 to a second computer system 24. For example, and without limitation, the second computer system 24 may include computing resources that allow it to reprocess the physiological data corresponding to the notable findings with greater accuracy than the mobile device 12. The second computer system 24 may produce a report and may send the results for clinical review (not shown).

The second computer system 24 may analyze differences between the results from the mobile device 12 and the results from the reprocessing by the second computer system 24, and may generate or retrieve new "patterns" (discussed below) to improve processing on the mobile device 12. The new patterns may be sent over the communications link 28 to the mobile device 12. The second system 24 may work cooperatively with the mobile device 12 to provide the high quality and timely detection of notable findings.

The sensors 16 may be attached to the body of the patient (or may be embedded in clothing next to the skin). The sensors 16 may provide physiological signals to a front-end 18 of the mobile device that typically may include one or more amplifiers, one or more filters, and one or more A/D converters. The mobile device 12 typically may be worn or carried on the body of the patient. The front end 18 may amplify and filter the analog signals and convert the analog signals to digital data for processing by a processing device 20 in the mobile device 12. The system arrangement 10 may be implemented in several different configurations as discussed below.

Communications between the second computer system 24 and mobile device 12 may be bi-directional. The mobile device 12 may record, analyze and/or report on patient physiological data, such as electro-cardiograph (ECG), blood pressure, respiration, temperature, EEG (brain waves), electromyography, etc. For example, and without limitation, the mobile device 12 may be configured to detect cardiac abnormalities in an ECG signal.

The second computer system 24 may maintain a large database 26 of physiologic patterns. The database 26 may store patterns, reference templates, and parameters for use in beat and rhythm classification by the mobile device 12 or second computer system 24. The second computer system 24 may maintain historical reference data on the subject, including for example, and without limitation, ECG strips, templates and reference data for future processing.

Initialization software to enable the mobile device 12 to communicate with the second computer system 24 may be downloaded to the mobile device 12. The second computer system 24 may configure the mobile device 12, and may provide software, parameters and reference data for use by the mobile device 12. The installation may take into consideration existing hardware and software configurations of the mobile device 12. The initial download may be, for example, and without limitation, a "Setup.exe" type application that selects and manages download of other components in the downloaded software. The second computer system may also transmit software updates to the mobile device.

Figure 2:
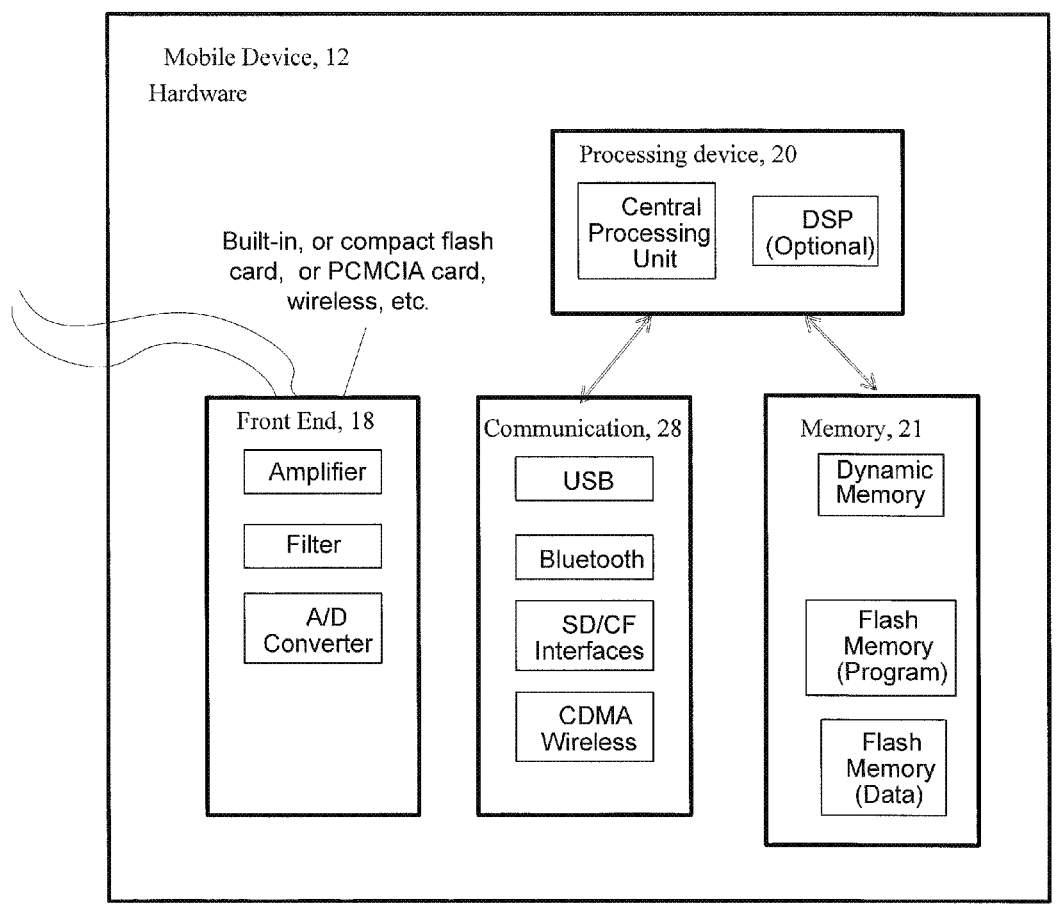
FIG. 2 is a block diagram of a mobile device.

Referring to FIG. 2, the mobile patient device 12 may include three functional components, as shown: a front end 18 that may condition and digitize signals sensed by the mobile device from a patient; a processing device 20 and associated support hardware to produce a computing device that may process the signals based on software and algorithms; and a communications path 28, such as a wireless link, that may allow the processor to communicate with the second computer system. The components may be grouped into a single device or may be configured as two or three separate devices. A patient may wear electrode sensors (FIG. 1) that may be attached to a lightweight patient cable assembly (not numbered). The other end of the cable may be attached to a compact card which may plug into a standard type slot, such as a compact flash slot or PCMCIA slot, on a computer.

For example, and without limitation, the card may include input processing circuits (front end 18) to amplify, filter and digitize the input signals from the electrode sensors, and also non-volatile flash memory 21 to store the ECG and other data. The card may plug into a standard slot on the processing device 20, for example, and without limitation, a PDA or handheld PC, which may perform the processing and communicate with the second computer system 24 over established wireless networks. In another embodiment, (not shown) the patient may wear a garment with built in sensors and a built-in front end 18 (e.g., amplifiers, filters, and analog to digital converters), for example, and without limitation, integrated ECG sensors that may permit less intrusive monitoring than conventional stick-on electrodes. The garment-based sensors may have a known and predictable electrode configuration. Garments with ECG sensors may have an associated identifier that may specify the ECG sensor and lead configuration. The configuration identifier may be encoded into the garment to allow it to be determined automatically by the patient module or base station. The identifier may use an encoding technology such as radio-frequency identification (RFID) or an electrically accessed circuit incorporated into the garment. Once the identifier is known, the mobile device 12 and the second system 24 may adapt the processing to the sensor configuration corresponding to the identifier.

Also for example, and without limitation, the front-end 18 may communicate with a mobile phone and/or computer that may be powered by a long-life battery or fuel cell. The mobile phone/computer may have a standard mobile operating system on it that may allow the patient to run standard applications. The mobile phone/computer may be initialized for the patient mobile device function by downloading an application that may configure the mobile phone and/or computer so that either or both devices may communicate with the front end and communicate over the wireless mesh or Internet.

Front End

The front end 18 may interface to the physiological sensors and may make available a stream of digital data. The sensors to which the front end 18 connects may include conventional sensors such as ECG electrodes, or advanced technology such as a garment that incorporates sensors into the fabric, as discussed above. For garment-based sensors, the front end may also be incorporated into the garment. The front end may be separate from the mobile computer, or the front end 18 may communicate with the mobile computer by wire or by a wireless connection such as Bluetooth. The front end may receive power from the mobile processor over a wire. The front end, when connected wirelessly, may save power and transmission costs by storing signals and then regularly transmitting the stored signals during a brief transmission interval. The front end may include memory to store digitized signals.

Mobile Processing Device

The mobile processing device 20 may analyze the signals and may communicate with the second computer system through the wireless link. The mobile processing device may be coupled to the front end 18. The mobile device 12 may include memory 21, including non-volatile memory such as flash memory, that may store the programs that run in the device and the digitized signals. The mobile processing device 20 and second computer system 24 may use a secure communication protocol or may encrypt data exchanged between the mobile computer and second computer system 24. The mobile processing device 20 and second computer system 24 may use efficient data streaming protocols to minimize network traffic, instead of protocols such as TCP/IP. The mobile processing device 20 may be a PDA or a wireless phone. The mobile processing device 20 may be or may include a specialized processor that may optimize signal-processing capabilities of the mobile device 12, such as a digital signal processor unit. The mobile processing device 20 may provide a user interface through which the user can interact with the mobile device, e.g., the mobile computer may be accessible using a browser. The user may review settings and may modify operation of the mobile device.

Communication Path

The communications path 28, such as a wireless link, may provide bi-directional connectivity that may allow the mobile device 12 to function as a networked computer. The wireless link 28 may use the Internet to communicate with the second computer system 24 or a wireless mesh to communicate to the second computer system 24. The wireless link may be integrated as part of a mobile phone or PDA.

The mobile device may record, analyze, and report on spatial parameters such as the patient's motion, physical orientation, and location as determined by global positioning systems in the device (not shown, but GPS may be common in a cell phone, for example). The mobile device may use the spatial parameters to determine whether a change in physiological data may be attributed to a change in physical orientation of the patient. The mobile device may use the signals from motion and physical orientation to detect that a patient has fallen down. The mobile device may be configured to report that event to the mobile device facility immediately. Prior to reporting, the mobile device may give the patient time to prevent the report, and may prompt the patient with a cue (e.g. sound, vibration) that, if responded to, may cancel the report.

The mobile device 12 may allow the patient to mark an occurrence of a symptom, including onset/offset, or to document activity. The mobile device may allow the patient to add a voice note to each mark, or to produce a mark by adding a voice note. The mobile device may be used by the patient to manually trigger a request for help. When reporting a potential emergency, the mobile device may communicate directly with a facility or system other than the second computer system.

Patterns

A pattern, as used herein for purposes of definition, may be a specification of characteristics, i.e., a form or model that may be used by the mobile device 12 and the second computer system 24 to compare to incoming ECG data. In some cases, a pattern may include new or updated software for execution by the mobile device 12. An exemplary pattern involving a model and specification of characteristics may be the pattern of a single heart beat (e.g., a "heart beat pattern").

The heart beat pattern may be represented by QRS samples of the signal, where each sample may be represented according to amplitude (relative to a reference level) and time of occurrence of a point in the pattern (relative to some point in the beat). For example, and without limitation, if the time of the Q peak is considered time zero, then the time for R is the time from Q to R. These relative measures may allow the heart beat pattern to be compared to newly detected beats, and to detect clinically significant episodes or events.

The heart beat pattern and other parameters, such as the beat width, may make up a "beat template," which may be derived from a number of similar beats. A beat template may be produced for each beat category (e.g., normal, ventricular, etc.). Newly detected beats may be compared to the beat templates from each beat category in order to classify the beats. For example, and without limitation, comparing a beat to a beat template may be a type of pattern matching.

Another type of pattern matching may be used for cardiac rhythm detection. The rhythm called bigeminy may be defined as having alternating normal "N" and ventricular "V" beats (N V N V . . . ). A rhythm template may represent bigeminy as eight (8) beats: (N V N V N V N V). Incoming beats may be compared to the bigeminy template to see if a bigeminy condition exists in the incoming beats.

Patterns may be represented as events in time, such as the QRS waveform or the pattern of beats described above. However, a pattern may not have to be described according to time. A pattern may be any specification of characteristics or a set of parameters. For example, an RR interval may be classified according to the "pattern" of its length. To perform pattern matching and classification of a signal, pattern matching criteria may be defined. Thus, in the above rhythm example, a beat may be classified as being either N (normal), V (ventricular), or possibly something else like fusion (in which case it would not match the given bigeminy rhythm).

Another type of pattern may be characterized as a rule. A rule may have a set of conditions and an action that is to be performed if the set of conditions is met. For example, a beat classification rule may be as follows: "if a beat is wide, classify it as ventricular." In this embodiment, the condition is "wide beat," and the action is to "classify beat as ventricular." This is an example of a classification rule. Other types of rules may include processing rules such as, for example, and without limitation, a rule to determine when to escalate a cardiac finding on the mobile device 12 and immediately notify the second system 24. A set of rules may be generated, e.g., by the second system for a specific condition or patient. At least a subset of those rules may be downloaded to the mobile device 12 for a specific condition or patient. The rules may affect subsequent processing by the mobile device 12.

Figure 3:
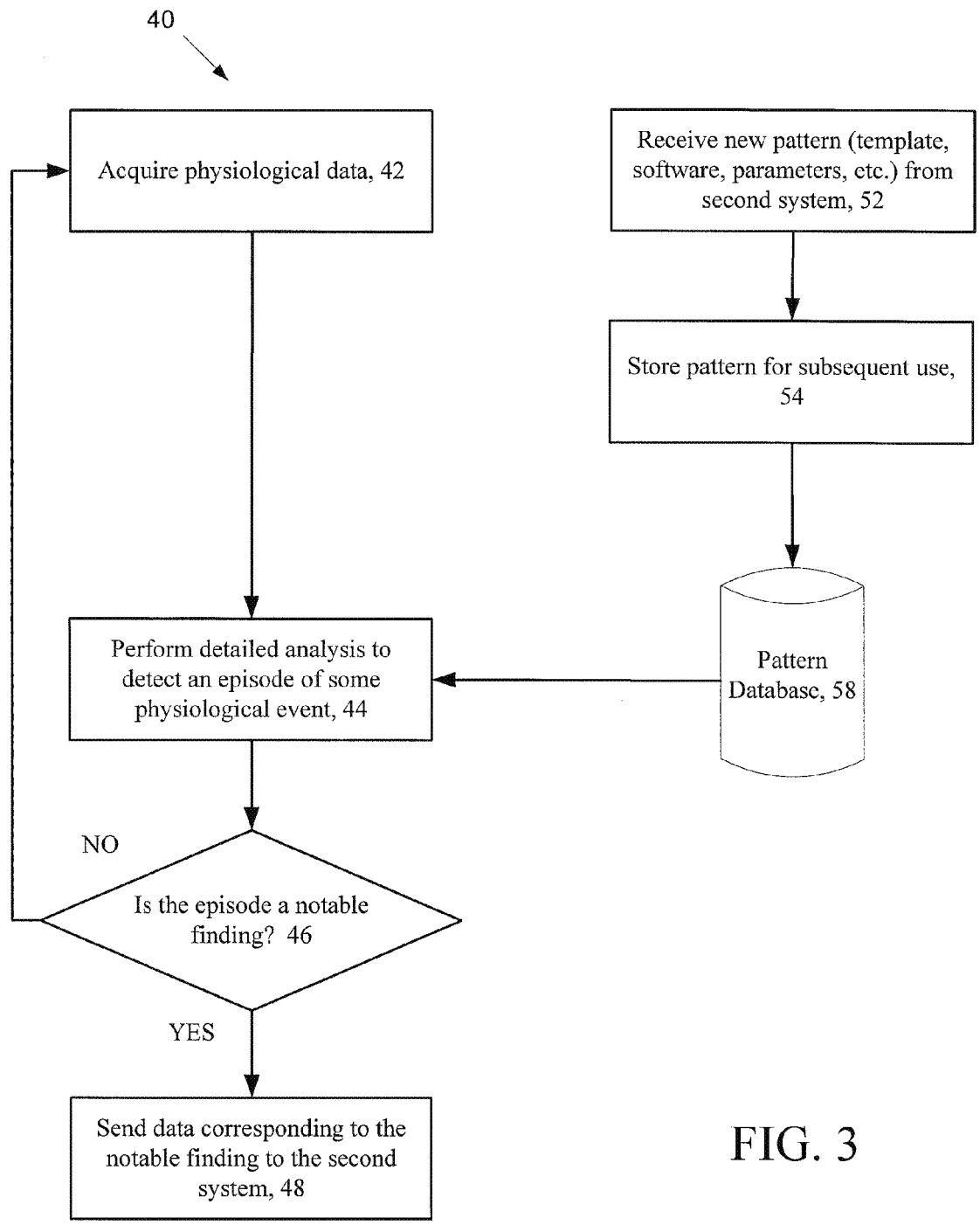
FIG. 3 is a flow chart detailing aspects of cooperative processing on a mobile device.

Referring to FIG. 3, a cooperative processing process 40 that occurs on the mobile device 20 is shown. The mobile device (FIG. 1) may acquire 42 physiological data from the front-end 18. The process 40 may perform a detailed analysis 44 of the data to detect an episode of some physiological event. If an episode was detected, the process 40 may determine 46 if the episode may be considered as a notable finding. For example, and without limitation, notable findings may include an episode which has been classified as a clinically important finding (such as atrial fibrillation); an episode that contains too much noise for the mobile device to successfully analyze; or a pattern that does not fit any of the templates in the mobile device. If the episode is not a notable finding, the process 40 may begin again. If the episode is considered a notable finding, the process 40 may send 48 the physiological data corresponding to the notable finding to the second system 24. The physiological data may be sent 48 either immediately after the notable finding was determined, or multiple notable findings may be stored and sent periodically.

For example, and without limitation, if the device 20 is to detect heart arrhythmias, then the physiological data may be ECG, and the detailed analysis 44 may be a cardiac arrhythmia detector. Notable findings for cardiac arrhythmias may include ventricular flutter, ventricular fibrillation, and/or atrial fibrillation. If a detected arrhythmia is determined to be a notable finding because it has been classified as, for example, atrial fibrillation, then the ECG corresponding to the episode of atrial fibrillation (i.e. 2 minutes of ECG) may be sent 48 to the second system 24. For example, and without limitation, if the episode of atrial fibrillation is 25 beats long, then a segment of ECG two minutes long that may include the 25 beats may be sent 48 along with an indication of the onset and offset of atrial fibrillation within the selected ECG.

The data corresponding to the notable finding sent in 48 may be data generated by different parts of the process 40. The example describes sending the ECG, which may be the raw physiological data input to the process 40. The input data may be sent so that the second system 24 may reprocess the same data with its better resources (e.g., more processing power and/or storage capacity). The process 40 also may send intermediate or final results of its analysis of the data, so that the second system 24 may improve the processing of the process 40, as follows.

The detailed analysis 44 may detect episodes of events using patterns, which could be, for example, and without limitation, beat templates, rhythm templates, and/or rules, as described above. These patterns may be stored on the processing device 20 in the pattern database 58. New patterns may be received 52 on the mobile device 20 from the second system 24. The new patterns may be stored 54 in the pattern database 58 to be used by the detailed analysis 44.

Figure 4:
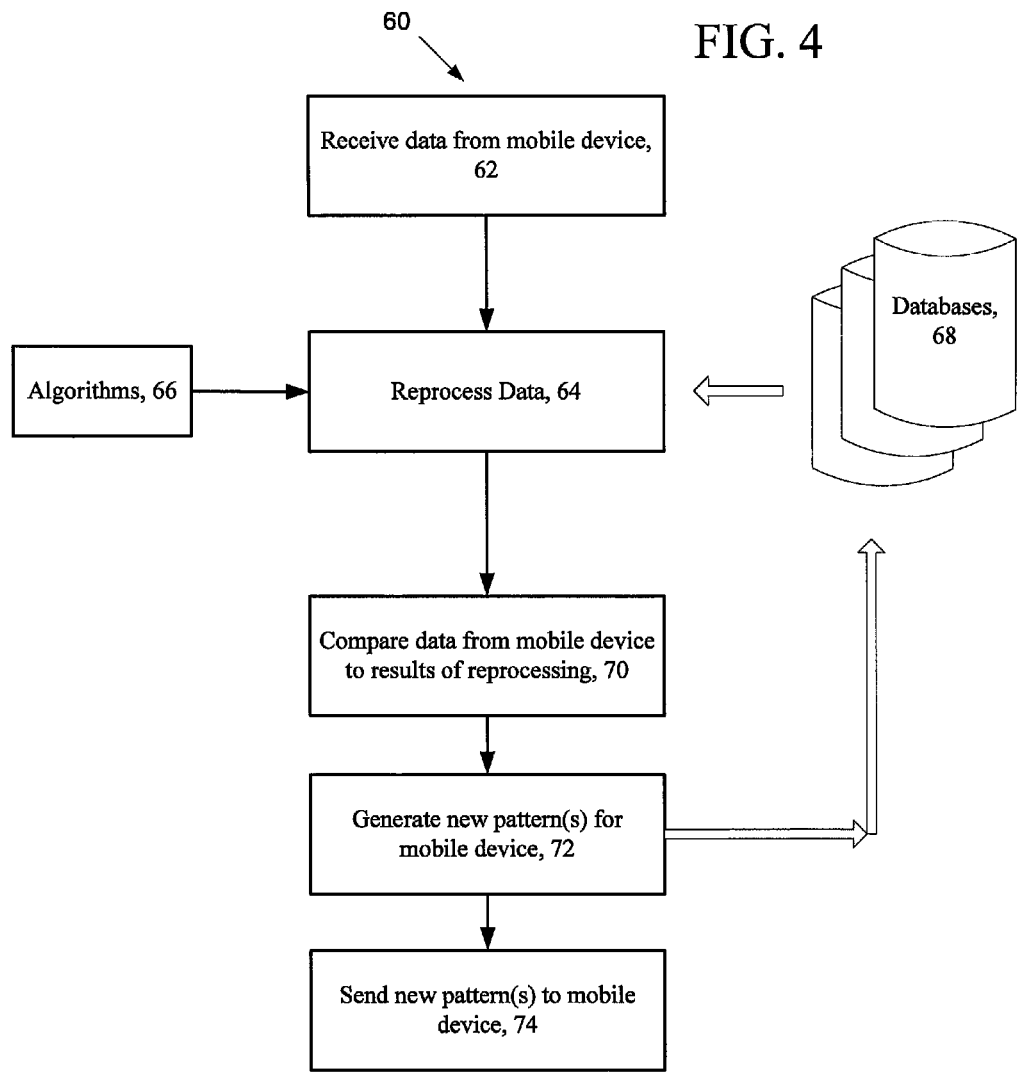
FIG. 4 is flow chart detailing aspects of cooperative processing on a second system.

Referring to FIG. 4, cooperative processing 60 that may occur on the second system 24 is shown. For example, and without limitation, the process 60 may receive data 62 from the mobile device 20, such as the raw physiological data that may be input to the mobile device 20. In addition, the data may include intermediate or final results of analysis on the mobile device 12. The data may be reprocessed 64 using more extensive resources than are available on the mobile device 12, such as for example and without limitation, a variety of algorithms 66, more powerful processors (not shown), and/or a larger set of databases 68. The reprocessed data may be compared 70 to the data received from the mobile device 12. If there are no significant differences, then the mobile device 12 may not be updated.

If significant differences are found, then the reprocessed results on the second computer system may be assumed more accurate, and those results may be used to generate 72 new patterns for the mobile device 12. The new patterns may be used to improve processing on the mobile device, such as for example, and without limitation, to make processing more accurate and/or more efficient; and/or to reduce communication time with the second computer system. The new patterns may be sent 74 to the mobile device 20, and may be stored in the databases 68 along with any relevant data, such as the raw physiological data that may be received from the mobile device 12.

As an example of the type of processing that may occur on the second system 24, assume again that the system 10 is a cardiac arrhythmia detector. The data received 62 from the mobile device may be ECG data as well as an indication of the onset and offset of the particular arrhythmia. Suppose the mobile device sends two minutes of ECG data with an indication of 25 beats of atrial fibrillation, and the reprocessing 64 also detects atrial fibrillation, but for a period of 10 beats. The comparison 70 may show a significant difference, and a new pattern may be generated 72 and sent 74 to the mobile device 20.

The databases 68 may store data for the specific patient wearing the portable device, and data that may have been compiled from many patients. For example, and without limitation, the databases may contain physiological data, derived data, rules, procedures, programs, and/or templates.

If the second system 24 detects a notable finding from the data sent by the mobile device 12, the system 24 may perform several actions (not shown) in addition to generating new patterns, including notifying clinical personnel and/or the patient of determined clinically notable findings. Some notifications may be low priority, and may be carried out in the form of daily updates to clinical personnel for review. If the second system 24 detects a more serious finding, the second system 24 may make the notification immediately, and may contact a physician or emergency services directly instead of the clinical review personnel.

The process 60 may include sending a new pattern to modify the mobile device's processing. Based on the analysis of the data, the second computer system 24 may direct the mobile device 12 to send additional data or to modify the operation of the mobile device 12 by changing what the mobile device 12 looks for, or to improve the processing by providing more appropriate reference data, processing rules, or new or revised patterns of other kinds.

Thus, processing workload may be split between the mobile device 12 and the second computer system 24. The balance may be adjusted to suit available mobile technology. For example, and without limitation, the mobile processor 20 may be a pre-processor for the second computer system 24. The mobile device 12 may receive operating parameters and reference data for algorithms executed on the mobile device 12, as well as executable code from the second computer system 24. The mobile device 12 may operate in standalone mode when access to the second computer system 24 is not available. During that time, the mobile device 12 may save notable findings and information in non-volatile memory. In typical operation, the mobile device 12 periodically rather that constantly may communicate data to the second computer system 24. More specifically, the mobile device may send periodic updates of information to the second computer system 24. Immediate contact with the second computer system 24 may occur only if there is a potentially serious event, or an event that needs the additional processing resources of the second computer system 24, rather than a notable finding.

Under normal operating conditions, the second computer system 24 may be in regular contact with the mobile device 12. Even when the mobile device 12 does not detect any findings that herald a possible problem, the mobile device 12 may send (or be asked to send) data. The data may be analyzed by the second computer system 24, which may have access to greater computational and/or database resources than the mobile device 12. If the second computer system 24 finds errors, it may send the mobile device 12 additional reference data and parameters to correct the processing, as discussed above. The intervals between data transmission may be controlled by the second computer system 24, and may take into account the clinical risk of the patient and/or the complexity of the signals being processed by the mobile device 12.

During cooperative processing, the selection of findings to look for and the threshold for detecting clinically notable findings may be governed and modified, as needed, by the second computer system 24. The second computer system 24 may conduct a detailed and thorough analysis that may use, for example, and without limitation, state of the art ECG analysis of the signals to determine whether the data may include a notable finding. A final examination and classification of the data may be performed by the second computer system 24. The second computer system 24 may determine a new pattern to send to the mobile device 12, based on the analysis, and may send the new pattern to the mobile device 12.

The mobile device 12 and second computer system 24 may work cooperatively and collaboratively as a hybrid of distributed processing. Cooperative processing may attempt to strike a balance between the processing requirements on the mobile device 12 and the amount of data that is sent to the second computer system 24 versus the need to perform high quality analysis.

Cooperative processing in the context of ECG analysis may be a hybrid between so called "Holter monitoring" and "event monitoring." In "Holter monitoring," a patient module may acquire the ECG data but may not analyze the data. After recording is complete, the data may be analyzed at a base station. The base station may identify clinically notable findings for review by clinical specialists. In "event monitoring," data selection may be performed in the patient module, either as the result of ECG analysis or due to a patient-initiated trigger. The selected ECG results may be transmitted or downloaded to a system at a central facility. In contrast, in cooperative processing, both the mobile device 12 and the second computer system 24 may play a role in processing acquired data and, as discussed either, may raise an alert to the patient or send a notification to a central facility.

Clinical Performance

The role of the mobile device 12 may be to advantageously exhibit relatively good sensitivity to potential events and not be too susceptible to false negatives; whereas the role of the second computer system 24 may be to advantageously improve the positive prediction capabilities of the system 10 by rejecting false positives, without decreasing the sensitivity of the system 10 by rejecting true positives.

Configurability

The system arrangement 10 may be configurable so that medical personnel can determine what types of episodes will be reported. The thresholds for reporting may be set low for a new patient, such that almost any abnormality may be reported. For patients with known abnormalities, the thresholds may be set to report and send the ECG data only when the abnormality is more severe than prior episodes of the same abnormality.

Reference Data

The second computer system 24 may send reference population data and parameters to the mobile device 12 as the cooperative processing executes in the mobile device 12 to make decisions as it processes the incoming ECG data.

The reference data and parameters may be sent at the start of monitoring or at any point during the monitoring.

The reference data may include some or all of the following information:

Parameters such as probabilities, rates, interval durations and amplitudes;

Templates of individual beat morphologies, as discussed below and sequences of beat types (such as the bigeminy pattern discussed above).

The reference data may be indexed according to characteristics, such as age, gender, height or weight. The second computer system may take into consideration the patient's characteristics when selecting the reference data. The reference ECG data may also be indexed according to the ECG lead configuration. If the patient's lead configuration is known, the second computer system may select or modify the reference ECG data to be more appropriate to specific sensor configuration. The reference data may be tailored to the specific patient and specific sensor configuration in order to advantageously improve analysis by the patient mobile device 12.

The reference population data may be used in processing by the second computer system, as described below. The data may include data related to patient-specific learning based on past monitoring sessions. For example, if a patient has had an intermittent bundle branch block, a template and characterization of the bundle branch block beat may be created by the system 10, and bundle branch block may be more confidently detected if it occurred during a new monitoring session.

Having a set of previously observed ECG patterns may advantageously make it easier to detect new patterns. For example, if a patient previously had bundle branch block, but there is a change in the extent of the block causing a significantly wider beat morphology, the change may be detected.

In the event that the mobile patient device detects a new beat type or an abnormality that is not already represented in its memory, the module may send the data to the second computer system 24. Doing so may allow the second computer system 24 to advantageously maintain a complete record of known ECG findings for the patient.

As with the population data, the patient-specific data may be indexed for the sensor configuration. The reference patient data, as with the reference population data, may be used by the second computer system 24 in processing of the data from the mobile device 12, as described below.

Conditions for In-Depth Analysis

Generally, the mobile device 12 may capture data from the patient and may process the data. The mobile device may send the data to the second computer system 24 for processing under certain conditions. The mobile device may send the data to the second computer system 24, when the mobile device 12 encounters an ECG pattern that has not been seen before or that has been seen infrequently. The mobile device 12 may send the data to the second computer system 24 when the mobile device encounters a transition to a new rhythm. For example, whenever the mobile device 12 detects an ECG patterns that seems like atrial fibrillation, the mobile device 12 may transfer a segment of the ECG data containing the onset of the detected pattern to the second computer system 24 for detailed analysis to determine if the segment fits the pattern of atrial fibrillation and, if it does, to determine the exact onset of the atrial fibrillation. The analysis performed by the second computer system 24 may involve detailed processing of the ECG to remove the effect of the QRST complex and to analyze the atrial activity.

Other conditions under which the mobile device 12 sends data to the second computer system 24 may include when the mobile device 12 falls behind making a determination on a segment of ECG data. The mobile device 12 also may send data to the second computer system 24 for trending or audit purposes at periodic intervals or at pre-specified times or conditions.

Cooperative processing as described above may allow for contrasting and comparing mobile device 12 and second computer system 24 results. For example, and without limitation, the second computer system 24 may have greater processing power than a mobile device 12 and, thus, the second computer system 24 may be better suited for in-depth analysis involving computationally intensive pattern recognition. The analysis performed on the second computer system 24 may compare the ECG against a large database of ECG records and patterns. For example, and without limitation, the database may include the patient's past ECG data and population data. This combination of greater power and larger available reference data may advantageously permit the second computer system 24 to perform rigorous in-depth analysis of the ECG to confirm findings, find new patterns and reject errors. The more powerful computing resources on the second system 24 may allow faster processing than in the mobile device 12, and less ECG data may need to be processed on the second system 24 because the mobile device 12 may only send a portion of all its findings to the second system 24.

Even though mobile processors are increasingly powerful, in-depth analysis by the mobile device 12 with existing processors would suffer the disadvantage of drawing significant power. Such a mobile device 12 may require larger batteries or more frequent re-charging, both of which would make the mobile device 12 more cumbersome to use. For the near-term, there exists a practical limitation on how much of the processing can be done by the mobile device 12. Likewise, existing wireless network capability, reliability, and cost make it prohibitive to stream all of the ECG data to the second computer system 24. Even if it were reasonable to do so, the economics of housing and supporting dedicated second computer systems 24 would likely be unfavorable, and would require a larger second computer system 24 than the cooperative processing approach described above. Furthermore, there would be an added cost because the real-time reliability of the second computer system 24, and network connections would need to feature higher throughput capacities.

Even as technology progresses and mobile processors become more powerful and more power efficient, and fuel cell technology provides increased "battery" life, the cooperative processing approach described above will remain useful. One reason is convenience. Patients may want and expect devices to continue to shrink in size, yet provide increasing functionality. Even though it may be possible in future years to do almost all of the ECG processing in a device that is the size of a present-day PDA, for instance, patients would likely not want to have devices that large. This may be especially true of those who are relatively healthy and are using the device for routine mobile monitoring as part of a general regimen of keeping healthy.

In a limited computing environment, the processing may be set to find representative events. One example is the problem of categorizing beat type templates under different body positions. Changes in body position (e.g. supine vs. upright) may cause a shift in the position of the heart, which usually changes the shape of the QRS complexes recorded by the different leads. A QRST template may be indexed by QRS electrical axis (or modified based on the QRS axis) so that two different QRST morphologies, which differ because the heart was in a different position, may be determined by the algorithm to be the same beat type.

Figure 5:
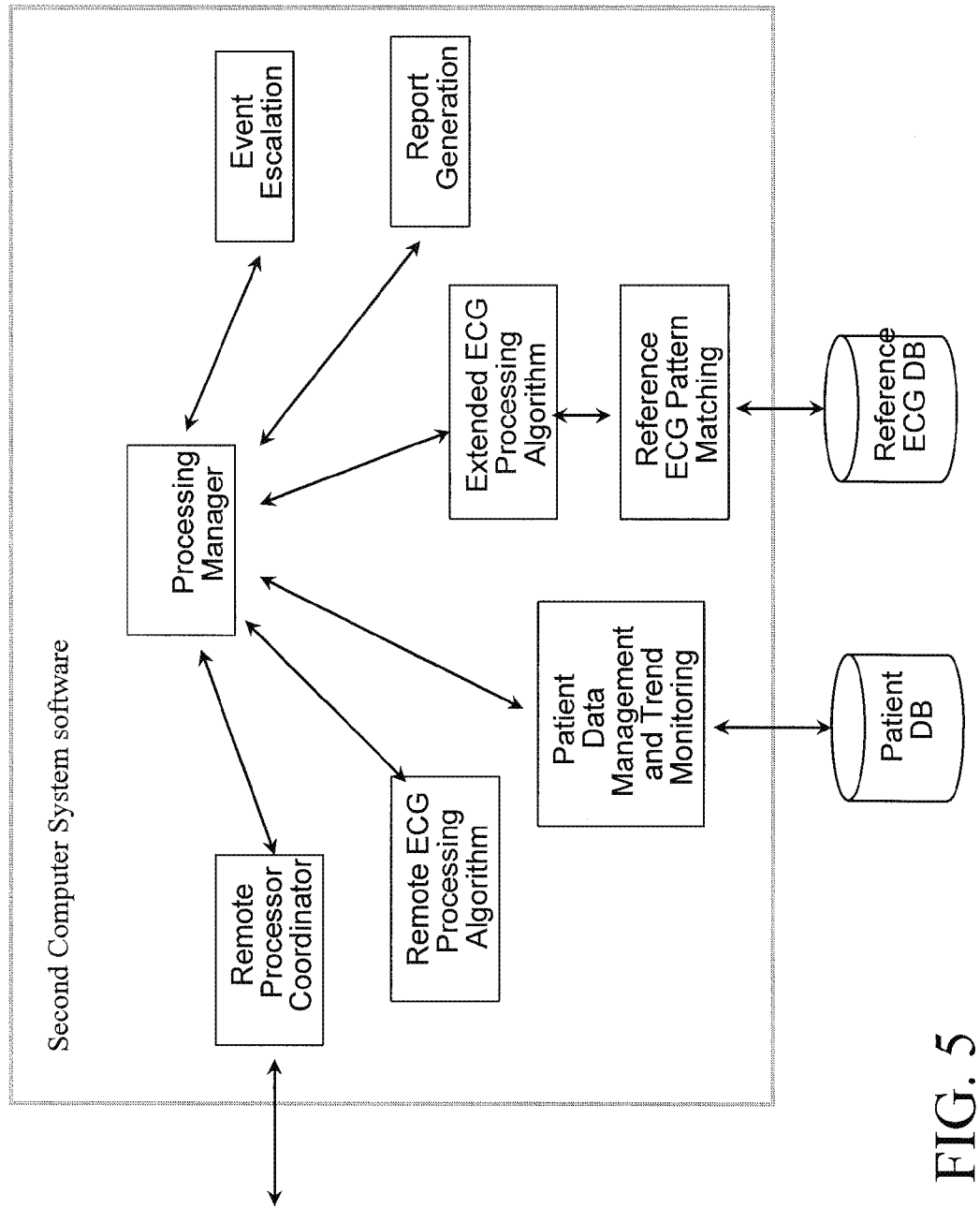
FIG. 5 is a block diagram of computing functions performed by the second computer system.

Referring to FIG. 5, the second computer system 24 may operate by itself or part of a larger facility including a server-farm. The second computer system 24 may be configured to include a processing manager, remote processor coordinator, and remote ECG processing algorithm manager. In addition, the second computer system 24 may include a patient data management and also a trend monitoring manager that interfaces with and manages the patient database. The second computer system 24 may include an extended ECG processing algorithm and a reference ECG Pattern Matching manager. The second system 24 also may include processes for report generation and event escalation.

The second computer system 24 may be implemented in many different ways. For example, and without limitation, the system 24 may be implemented as a single computer system that is network enabled at a patient's home. Such a private second computer system 24 may maintain a detailed record of ECG findings over time for the patient, and may be configured to advantageously escalate specific types of findings by sending data to another second computer system at a clinical monitoring facility, or by generating a fax, e-mail, or other communication artifact to be sent to medical personnel. A single second computer system may be capable of concurrently servicing more than one patient mobile device.

The second computer system 24 at a monitoring facility may be part of a large facility that can establish a session with the mobile device 12 so that the same server continues to interact with the mobile device 12. The second computer system at a monitoring facility may be configurable on a per-patient basis to specify escalation rules for different types of findings.

The second computer system 24 may receive the voice notes from the mobile device 12 discussed above. For example, and without limitation, the second computer system may use speech to text technology to produce a text note from the speech note generated by the mobile device 12 to associate with the data. The second computer system software may proactively request the signals from the patient to develop a representative sampling of the ECG over time. The second computer system 24 may interact with a database to keep a historical record of part or all of the data that it receives from the mobile device. The second computer system may analyze the historical ECG record to produce beat templates and rules relevant to the patient.

The second computer system 24 may have access to any of the data in the mobile device 12. In addition, the second computer system 24 may send, as appropriate, updated parameters that determine the general operation of the mobile device 12, including the types of episodes that are detected and reported. The second system may send corrections to internal classifications or to templates produced and held by the mobile device 12. The second system 24 may send reference data including ECG beat templates, and/or historical data for the patient (for example, and without limitation, identifying what is normal for that patient). The second system 24 may send instruction intended for the patient.

Templates

Exemplary templates may be generated for various functions and processing performed by the system. The templates may be adjusted and used by the mobile device and the second computer system 24 based on findings observed during processing of the ECG signals.

Data Acquisition

For example, and without limitation, a subject may wear ECG electrodes or an undergarment with integrated ECG sensors. For routine monitoring of one or two channels of ECG, signals may usually be acquired by the ECG module, which may amplify the ECG signal and may filter it to preserve frequencies in the range of 0.05 to 100 Hz. The ECG signal may be sampled typically at a frequency in the range of 250 to 360 Hz. The digitized ECG may be transferred to the mobile processor for processing. The mobile processor may save the data in its flash memory.

Ventricular and Atrial Activity Processing

Ventricular processing may involve some or all of the following actions:

Bandpass filtering of the ECG in a specified frequency range of, for example, and without limitation, 5-40 Hz to advantageously emphasize the signal content of the QRST complex;

Multi-channel peak detection to advantageously identify candidate QRS complexes in the filtered signal;

Measurement of the subject's physical orientation to detect shift in body position; and Comparison of detected beats against templates derived from live ECG data and against reference templates provided by the second computer system 24.

If the subject's body position has changed, the comparison against the live ECG templates may consider the change in the QRS axis. The template may keep track of QRS shape as a function of the QRS axis.

Reference templates may include QRS axis information. The template matching may be restricted to templates that have a QRS axis similar to the current live ECG. Or the reference template may be transformed to make the QRST axis comparable with the live ECG data.

When a new QRS morphology is found, ECG preceding and following may be sent by the mobile device 12 to the second computer system 24 for in-depth analysis. The second computer system 24 may send back information that includes templates or parameters that may be used in classification of QRS morphologies.

Atrial Activity Processing may involve some or all of the following actions:

Preliminary classification of the beat based on template matching;

Multi-channel P-wave detection to look for individual P-waves preceding QRS complex. Comparing each P-wave against templates derived from recent beats and against reference templates provided by the second computer system 24. Producing a measure of each P-waves significance based on the template match and a signal-to-noise;

Additional processing (if single P-wave is not found and if the device is keeping up with real-time signals) may involve some or all of the following actions:

Adaptively subtracting the QRST complex by subtracting out the matching QRST template; and P-wave detection in the QRST interval to identify a P-wave.

Beat Classification

Beat classification may determine whether a beat is of atrial, junctional or ventricular origin. The processing may involve some or all of the following actions:

Producing timing and morphology measures of the beat;

Measuring how well the measures of (P)QRST morphology and timing measures match predefined parameters sets;

Default parameters sets based on conventional clinical definitions of ECG analysis;

Customized parameter sets may be supplied by the second computer system 24 based on past ECG or based on other data obtained from the subject. These may replace or augment the default parameter sets;

Measuring the correlation of an observed (P)QRST to (P)QRST templates. These measures may include the following: Similarity of the QRST to an existing QRST template duster that may be either derived from the live ECG data or provided by the second computer system 24 based on prior ECGs; Similarity of the P-wave (if one has been detected) to an existing P-wave template cluster and whether that template is associated with the QRST duster; Whether the (P)QRST template duster has been definitively classified as atrial, junctional or ventricular origin; and Measuring how well a (P)QRST for the most recent N beats matches previously observed patterns for N beats.

The matching may include absolute and heart-rate-normalized timing intervals of the QRS complexes and P-waves, along with the clustering measures of the QRS complexes and P-waves.

The number (N) of beats compared may range from 2 to 8 or more based on how well the processing is able to keep up with the real-time signals.

The second computer system 24 may provide the mobile processor with previously classified multi-beat patterns to use as reference data. The mobile processor may limit the number of patterns compared based on the available processing time.

Updating of templates based on the classification to include the contribution of QRS complexes put into the template duster. Clusters may be produced, merged or classified based on rules in the mobile processing algorithm or based on information sent by the second computer system 24.

Producing an audit trail that can be used (if necessary) by the second computer system 24 to review the decisions made by the mobile processor.

Rhythm Classification

Rhythm classification may involve looking for clinically recognized rhythm patterns in a sequence of beats. Multiple rhythm classifications may be determined for a set of beats, each classification having an associated confidence measure and clinical severity.

Rhythm and Event Matching (Hypothesis Testing)

The observed sequence of beats and their associated measures may be compared against reference data. For example, and without limitation, the reference data may include patterns derived from a general population database. Also for example, and without limitation, the reference data may include patterns identified for the subject. The comparison may be based on a set of vectors including measurements of the P-waves, atrial activity and QRST complexes that comprise the sequence of beats.

Implementations

The invention may be implemented in digital electronic circuitry, or in computer hardware, firmware, software, or in combinations thereof. An apparatus of an embodiment of the invention may be implemented in a computer program product tangibly embodied in a machine-readable storage device for execution by a programmable processor. Method actions may be performed by a programmable processor executing a program of instructions to perform functions of the invention by operating on input data and generating output.

The invention may be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Suitable processors may include, by way of example, both general and special purpose microprocessors. Generally, a processor may receive instructions and data from a read-only memory and/or a random access memory. Generally, a computer may include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD_ROM disks. Any of the foregoing may be supplemented by, or incorporated in, ASICs (application-specific integrated circuits).

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus the scope of the invention should be determined by the appended claims and their legal equivalents, and not by the examples given.

That which is claimed is:

1. A system comprising:
circuitry to receive information from a mobile device including physiological data related to a patient;

circuitry to analyze the physiological data using at least one pattern, defined as a detected pattern, to detect a notable finding in the physiological data, wherein the detected pattern comprises a rule that has a set of conditions and an action to perform if the set of conditions is met;

circuitry to determine at least one pattern to send to the mobile device, defined as a determined pattern, based on the analysis of the physiological data; and circuitry to send the determined pattern to the mobile device.

2. The system of claim 1 wherein the determined pattern includes the parameters of a mathematical model.

3. The system of claim 1 wherein the determined pattern includes a template derived from historical physiological data.

4. The system of claim 1 wherein the circuitry to analyze the physiological data includes circuitry to compare the analyzed physiological data to templates from categories of physiological events in order to classify the physiological data.

5. The system of claim 1 wherein sending the determined pattern includes sending software.

6. The system of claim 1 wherein the detected pattern comprises a first QRST template representative of a supine subject.

7. The system of claim 1 wherein the detected pattern comprises a second QRST template representative of an upright subject.

8. The system of claim 1 wherein the determined pattern is further based on the analysis of patient characteristics selected from the group consisting of clinical information for the patient and demographic information for the patient; and wherein the determined pattern is sent to initialize the mobile device.

9. The system of claim 1 wherein the determined pattern comprises software for execution by the mobile device.

10. The system of claim 1 wherein the rule is selected from the group consisting of a classification rule, a processing rule, and a set of rules generated for a specific condition.

11. An arrangement comprising:

a first system provided by a mobile device for processing physiological data related to a patient, the mobile device adapted to execute a process for using at least one pattern to detect a notable finding in the physiological data and for sending the notable finding to a second system;

wherein the second system is adapted to execute a process for analyzing the notable finding, for determining at least one new pattern to send to the mobile device, and for sending the at least one new pattern to the mobile device; and wherein the at least one new pattern comprises a rule that includes a set of conditions and an action to perform if the set of conditions is met.

12. The arrangement according to claim 11 wherein the at least one new pattern includes parameters of a mathematical model.

13. The arrangement according to claim 11 wherein the process for determining the at least one new pattern includes deriving a template from historical physiological data.

14. The arrangement according to claim 11 wherein the process to send the at least one new pattern includes sending software to the mobile device.

15. The arrangement according to claim 11 wherein the process for determining the at least one new pattern includes selecting user characteristics from at least one of clinical information for the patient and demographic information for the patient; and wherein the process to send the at least one new pattern includes sending the user characteristics to initialize the mobile device.

16. A method comprising:

receiving a first notable finding from a mobile device, wherein the mobile device is configured to analyze physiological data related to a patient;

analyzing the first notable finding using a first pattern to detect a second notable finding;

determining a second pattern to send to the mobile device based on the second notable finding; and sending the second pattern to the mobile device.

17. The method according to claim 16 wherein the second pattern includes parameters of a mathematical model.

18. The method according to claim 16 further comprising:

comparing the analyzed physiological data to templates from categories of physiological events in order to determine the first notable finding.

19. The method according to claim 16 wherein the second pattern comprises a rule, the method further comprising generating the rule for at least one of a specific condition and the patient.

20. The method according to claim 16 wherein the second pattern includes a template derived from historical physiological data.

21. The method according to claim 16 wherein the second pattern includes software.

22. The method according to claim 16 wherein the second pattern includes user characteristics selected from the group consisting of clinical information for the patient and demographic information for the patient, and wherein sending the second pattern further comprises sending the user characteristics to initialize the mobile device.

* * * * *